(12) United States Patent
Seyr et al.

(10) Patent No.: US 9,278,013 B2
(45) Date of Patent: Mar. 8, 2016

(54) DEVICE AND METHOD FOR CONTROLLING AN ARTIFICIAL ORTHOTIC OR PROSTHETIC JOINT

(75) Inventors: Martin Seyr, Vienna (AT); Philipp Kampas, Vienna (AT); Sven Zarling, Duderstadt (DE)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 2 days.

(21) Appl. No.: 13/508,203

(22) PCT Filed: Nov. 12, 2010

(86) PCT No.: PCT/EP2010/006892
§ 371 (c)(1),
(2), (4) Date: May 4, 2012

(87) PCT Pub. No.: WO2011/057791
PCT Pub. Date: May 19, 2011

(65) Prior Publication Data
US 2012/0215323 A1 Aug. 23, 2012

(30) Foreign Application Priority Data

Nov. 13, 2009 (DE) .......................... 10 2009 052 890

(51) Int. Cl.
| | |
|---|---|
| *A61F 2/64* | (2006.01) |
| *A61F 2/60* | (2006.01) |
| *A61F 2/68* | (2006.01) |
| *A61F 2/70* | (2006.01) |
| *A61F 5/01* | (2006.01) |
| *A61F 2/50* | (2006.01) |
| *A61F 2/76* | (2006.01) |

(52) U.S. Cl.
CPC . *A61F 2/64* (2013.01); *A61F 2/605* (2013.01); *A61F 2/68* (2013.01); *A61F 2002/5003* (2013.01); *A61F 2002/5033* (2013.01); *A61F 2002/6818* (2013.01); *A61F 2002/704* (2013.01); *A61F 2002/7615* (2013.01); *A61F 2002/7625* (2013.01); *A61F 2005/0169* (2013.01); *A61F 2005/0188* (2013.01)

(58) Field of Classification Search
None
See application file for complete search history.

(56) References Cited

U.S. PATENT DOCUMENTS

| | | | |
|---|---|---|---|
| 5,383,939 | A | 1/1995 | James |
| 6,955,692 | B2 | 10/2005 | Grundei |

(Continued)

FOREIGN PATENT DOCUMENTS

| | | |
|---|---|---|
| CN | 1074109 A | 7/1993 |
| DE | 102006021802 A1 | 11/2007 |
| DE | 102007053389 A1 | 5/2009 |

(Continued)

OTHER PUBLICATIONS

PCT International Search Report for International Patent Application No. PCT/EP2010/006892, mailed Mar. 2, 2011.

*Primary Examiner* — David H Willse
(74) *Attorney, Agent, or Firm* — Holland & Hart

(57) ABSTRACT

The invention relates to a method and device for controlling an artificial orthotic or prosthetic joint of a lower extremity with a resistance device to which at least one actuator is associated, via which the bending and/or stretching resistance is changed depending on sensor data. During the use of the joint, status information is provided via sensors. According to the invention, the inertial angle of an thigh part is measured and the resistance is reduced, when the thigh part is at least 45° to the vertical and/or the knee angle is greater than 45°.

17 Claims, 1 Drawing Sheet

(56) References Cited

U.S. PATENT DOCUMENTS

| | | |
|---|---|---|
| 2003/0125814 A1 | 7/2003 | Paasivaara et al. |
| 2007/0083272 A1* | 4/2007 | Van De Veen et al. .......... 623/39 |
| 2010/0228360 A1 | 9/2010 | Pusch et al. |
| 2010/0305716 A1 | 12/2010 | Pusch et al. |
| 2011/0087339 A1 | 4/2011 | Pusch et al. |

FOREIGN PATENT DOCUMENTS

| | | | |
|---|---|---|---|
| DE | 102008008284 A1 | 8/2009 | |
| EP | 1237513 | 6/2001 | |
| EP | 1447062 A2 | 8/2004 | |
| GB | 2 367 753 A * | 4/2002 | ................ A61F 2/64 |
| WO | 0143669 A1 | 6/2001 | |

* cited by examiner

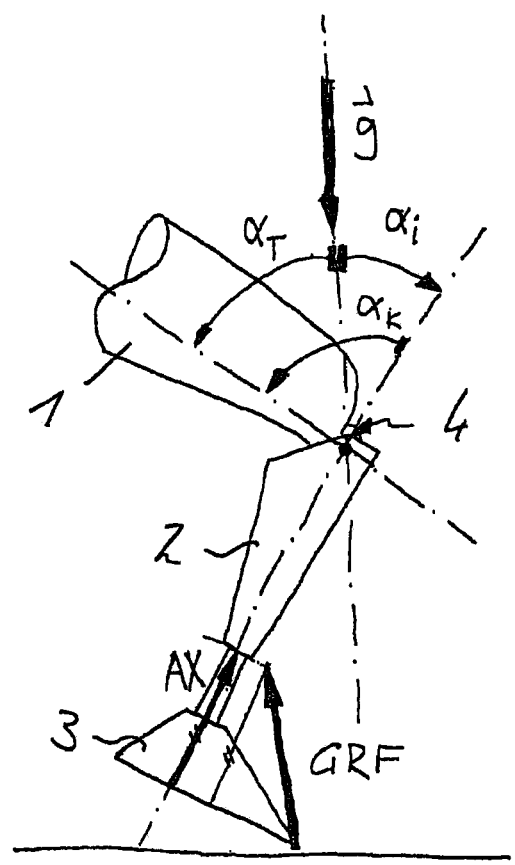

DEVICE AND METHOD FOR CONTROLLING AN ARTIFICIAL ORTHOTIC OR PROSTHETIC JOINT

TECHNICAL FIELD

The invention relates to a method and an appliance for controlling an artificial orthotic or prosthetic joint of a lower extremity with a resistance device to which at least one actuator is assigned, via which actuator the flexion and/or extension resistance is changed depending on sensor data, with status information being made available via sensors during the use of the joint. The appliance and the method are suitable in particular for controlling an orthotic or prosthetic knee joint, although the invention is also applicable to hip joints or ankle joints.

BACKGROUND

Artificial joints, in particular knee joints, for orthoses or prostheses have an upper attachment part and a lower attachment part, which are connected to each other via a joint device. In the case of a knee joint, the upper attachment part has seats for a thigh stump or a thigh rail, whereas the lower attachment part has a lower leg socket or a lower leg rail. In the simplest case, the upper attachment part is connected to the lower attachment part pivotably by a monoaxial joint. It is only in exceptional cases that such an arrangement is sufficient to ensure the desired result, for example a supporting action when used in an orthosis, or a natural gait pattern when used in a prosthesis.

To ensure that the different requirements during the various phases of a step or during other actions are satisfied or supported in a way that is as natural as possible, resistance devices are made available that provide a flexion resistance or an extension resistance. By means of the flexion resistance, it is possible to establish how easily the lower attachment part can pivot relative to the upper attachment part in the direction of flexion. In a knee joint, therefore, the flexion resistance is used to establish how easily the lower leg socket or the lower leg rail swings back in relation to the thigh socket or the thigh rail when a force is applied. The extension resistance brakes the forward movement of the lower leg socket or of the lower leg rail and can form an extension limit stop. In other types of joints, for example the hip joint or the ankle joint, these observations apply correspondingly to the kinematic relationships.

With adjustable resistance devices, it is possible to adapt the respective flexion and/or extension resistance to the user of the prosthetic or orthotic device or to different walking or movement situations, so as to be able to provide a suitable resistance under changing conditions.

DE 10 2008 008 284 A1 discloses an orthopedic knee joint with an upper part and, arranged pivotably on the latter, a lower part which is assigned several sensors, for example a flexion angle sensor, an acceleration sensor, an inclination sensor and/or a force sensor. The extension stop is adjusted according to the sensor data that are determined.

DE 10 2006 021 802 A1 describes a control system of a passive prosthetic knee joint with adjustable damping in the direction of flexion, for adaptation of a prosthetic device having upper attachment means and a connector element to an artificial foot. The adaptation is made to climbing stairs, wherein a low-moment lifting of the prosthetic foot is detected, and the flexion damping in a lifting phase is lowered to below a level that is suitable for walking on the flat. The flexion damping can be increased depending on the change in the knee angle and depending on the axial force acting on the lower leg.

DE 10 2007 053 389 A1 describes a method and an appliance for controlling an orthopedic joint of a lower extremity with at least one degree of freedom, having an adjustable actuator by which an orthopedic device, comprising upper means of attachment to a limb and an orthopedic joint arranged in an articulated manner distally from the attachment means, is adapted to walking situations that deviate from walking on the flat. Several parameters of the orthopedic device are detected via sensors, the detected parameters are compared with criteria that have been established on the basis of several parameters and/or parameter profiles and are stored in a computer unit, and a criterion is selected that is suitable on the basis of the detected parameters or parameter profiles. Flexion resistances, movement ranges, drive forces and/or the profiles thereof are established in accordance with the selected criterion, in order to control special functions that deviate from walking on the flat. A tilt angle of a part of the orthopedic device in space and/or a profile of a change in tilt angle of a part of the orthopedic device can be used as parameter.

EP 1 237 513 B1 describes a prosthesis or orthosis with a control device and, coupled thereto, a sensor which detects an inclination angle relative to a fixed line of a part connected to a joint. On the basis of the inclination angle data, the movement properties of the joint are changed, i.e. the joint is braked or released.

It has proven useful that knee joints offer a high degree of resistance in the stance phase during walking or also during standing, wherein the joint is not completely blocked. In this case, bending of the joint during standing is prevented by the fact that the force vector lies in front of the joint axis and thus forces the joint to the extension limit stop.

A non-locking of the joint in the standing situation has the advantage that the user still has possible ways of intervening in the joint movement. For example, should he be standing on stairs and lose his balance, a locked joint would cause him to fall without any control, whereas he is still able to bend a joint with a high resistance by means of the stump force. He can thus minimize the consequences of a fall or avoid falling altogether. The resistance also makes it easier to maneuver the joint in confined spaces and to sit down. Sitting down is made easier by the fact that the resistance provides support against the joint giving way too quickly. The resistance applied against the joint giving way too quickly would otherwise have to be applied by the side not fitted with a prosthesis, i.e. the healthy leg.

If a prosthesis or orthosis user is in a seated position, the situation can arise whereby the flexion resistance and/or the extension resistance is so high that comfortable sitting is not possible. While sitting, it is often necessary and convenient to have free mobility of the joint, such that the small movements made while sitting can be performed without problems.

SUMMARY

The object of the present invention is therefore to make available an appliance and a method by which it is possible to detect a seated state and to adapt the resistance of the joint to the seated situation.

According to the invention, this object is achieved by a method having the features of the main claim and by an appliance having the features of the additional independent claim. Advantageous embodiments and developments are set forth in the dependent claims.

In the method according to the invention for controlling an artificial orthotic or prosthetic joint of a lower extremity, a resistance device is provided to which at least one actuator is assigned, via which actuator the flexion and/or extension resistance is changed depending on sensor data. Status information is made available via sensors during the use of the joint.

The inertial angle of a thigh part is measured, and the resistance is reduced when the thigh part is at least 45°, in particular at least 70°, to the vertical and/or the knee angle is greater than 45°, in particular greater than 80°. The vertical is regarded as the direction of gravity, while the knee angle is the angle present between the upper attachment part and the lower attachment part of the knee joint, starting from an extended position in which the knee angle is 0°. The greater the flexion of the lower attachment part relative to the upper attachment part, the greater the knee angle becomes. When the seated state is detected, the prosthesis or orthosis can be more easily maneuvered if the resistance is reduced, preferably both in the extension direction and also in the flexion direction, and, if appropriate, the resistance device can be changed such that the additional resistance goes toward zero. Sitting is detected by measuring the inertial angle of the thigh part, that is to say the absolute angle of the thigh part relative to the vertical. If the inertial angle of the thigh part is substantially horizontal, that is to say at least 70° to the vertical, it can be assumed that the prosthesis user is seated or just about to sit down. Alternatively or in addition, the knee angle can also be used to assess the seated state. If the knee angle is greater than 80°, it can be assumed that a seated position has been adopted. The knee angle can also be used alone as the decisive variable for the control system, and, similarly, the inertial angle of the thigh part can also suffice to determine a seated position.

In a variant of the invention, provision is made that the resistance is reduced when the ground reaction force reaches or is below a threshold value. For this purpose, provision is made that the ground reaction force on the prosthesis or orthosis is measured. When the ground reaction force reaches or is below the fixed threshold value, because the seated position means that only a small part of the otherwise customary weight force is exerted on one of the components, for example the lower leg part, the joint or the prosthetic foot, it is possible for the resistance to be reduced.

It is possible and intended that, after reaching the threshold value of, for example, at least 45° for the inertial value of the thigh part and/or of the knee angle, the resistance is reduced continuously with the increasing angle. This serves as an aid to sitting down, such that the prosthesis or orthosis user, as a result of a high flexion resistance, does not first have to take up the full weight via the leg not fitted with a prosthesis. For example, if the thigh part is at an angle of 45° to the vertical, the flexion resistance can be reduced continuously, such that it is easier to sit down.

The inertial angle of the thigh part can be determined directly, i.e. by a corresponding sensor device on a thigh part, or from the inertial angle of a lower leg part and a joint angle, which is present between the lower leg part and the thigh part.

In a development of the invention, provision is made that the resistance is reduced only when the thigh part is located for a defined period of time in the inclined position, i.e. starting from an angle of ca. 45°, in particular 70°, to the vertical. This avoids an abrupt or even continuous reduction of the flexion resistance and/or the extension resistance taking place when the approximately horizontal position of the thigh part is briefly reached. A time function is thus present which permits a reduction in the resistance only after a defined time has elapsed. The time-controlled change in the resistance as a function of the duration of the almost horizontal position of the thigh part affords additional safety. A corresponding time-controlled change can also take place on the basis of the knee angle, such that the reduction in resistance is carried out only when the knee angle has a defined minimum value for a defined period of time.

In a development of the invention, provision is made that, after the reduction, the resistance, in particular the flexion resistance, is increased depending on a change of joint angle and/or a change of inertial angle, in order to provide an aid to standing up. When a user of the prosthesis or orthosis makes to stand up, there is the danger that the standing position will not easily be reached. In order to prevent falling back into the seated position without a resistance device, it is detected whether the joint angle and/or the inertial angle changes, particularly in the sense of extension of the joint and approximation of the thigh part to the vertical. If this is the case, the resistance, in particular the flexion resistance, is increased.

A reduction in the resistance may be suppressed if a change of joint angle is determined, i.e. if the device is not in a static or an approximately static state. It is possible in this way to provide an aid to standing up or an aid to sitting down.

If sitting has been detected and the resistance has been reduced, the control system can go into an energy-saving mode in which, for example, the clocking is slowed down or individual sensor values are not retrieved until it is established, on the basis of other sensor values, that the prosthesis user has left the seated position. Likewise, unused consumer elements can be switched to a stand-by state, such that the energy consumption as a whole is reduced.

To provide increased safety, a plurality of control algorithms may be present which, on the basis of measured values of different devices for detecting angles and forces, operate in such a way that, if a device for detecting angles and forces fails, the other measured values can be used to control the change in the extension and/or flexion resistance. It is thus possible for a redundancy to be built up. The algorithms can operate with measured values deriving from different groups of devices for detecting angles and forces, wherein individual overlaps can be provided within the groups such that, if a device for detecting angles and forces fails, the other measured values can be used to control the change in the extension and/or flexion resistance via other algorithms. The redundance of the control possibilities provides increased safety against failure of the prostheses or orthoses.

In the appliance according to the invention for carrying out the above-described method, provision is made that an adjustable resistance device is present, which is arranged between two mutually articulated components of an artificial orthotic or prosthetic joint of a lower extremity, wherein a control device and sensors are present, which detect an inertial angle of a component and/or a joint angle of the appliance. An adjustment device is provided, by means of which a position-dependent change of resistance can be activated and/or deactivated, so as to be able to actively switch on and off the special sitting function and the resistance reductions following the detection of the seated state.

BRIEF DESCRIPTION OF THE DRAWINGS

An exemplary embodiment of the present invention is explained below by way of a drawing, in which:

FIG. 1 shows a schematic view of a device according to an exemplary embodiment of the present invention.

DETAILED DESCRIPTION

An illustrative embodiment of the invention is explained in more detail below with reference to the attached FIGURE. In the single FIGURE, a prosthesis is shown schematically in a seated position. The prosthesis has a thigh part 1 and a lower leg part 2, which are connected pivotably to each other via a prosthetic knee joint 4. A prosthetic foot 3 is arranged on the lower leg part 2. The lower leg part 2 also has a resistance device and an actuator which, on the basis of sensor data evaluated by a control unit, adjusts the extension or flexion resistance to an extension or flexion movement of the thigh part 1 relative to the lower leg part 2. When the prosthesis user is in a seated position, it is convenient if the extension resistance and the flexion resistance of the resistance device are low, such that the movements that are made during sitting, and that generally have a low range of movement, can be performed without any impediment.

To be able to perform the reduction in resistance automatically, provision is made that the seated state is detected. For this purpose, provision is made that the inertial angle $\alpha_T$ and/or the knee angle $\alpha_K$ are measured. The inertial angle $\alpha_T$ of the thigh part 1 is measured with respect to the vertical, which is assumed to act in the direction of gravity. In the FIGURE, this is indicated by the gravitational vector g. The reference variable adopted for the inertial angle $\alpha_T$ is the longitudinal axis of the thigh part 1 passing through the pivot axis of the prosthetic knee joint 4. The longitudinal axis corresponds approximately to the orientation of a natural thigh bone and extends substantially centrally with respect to the thigh part 1, which is generally designed as a thigh socket.

The knee angle $\alpha_K$ lies between the longitudinal extent of the lower leg part 2 and the longitudinal extent of the thigh part 1. Here too, the longitudinal extent of the lower leg part 2 passes through the joint axis of the prosthetic knee joint 4. The inertial angle $\alpha_T$ of the thigh part 1 can be calculated from the inertial angle $\alpha_i$ of the lower leg part 2 and the knee angle $\alpha_K$, wherein, according to the FIGURE, the inertial angle $\alpha_T$ of the thigh part 1 is obtained from the difference between the knee angle $\alpha_K$ and the inertial angle $\alpha_i$ of the lower leg part 2.

The ground reaction force GRF or the axial force AX, which represents that part of the ground reaction force in the direction of the lower leg part 2, can also be determined in order to decide, on the basis of the forces present, whether or not the prosthesis user is in a seated position.

Provision is made that the reduction in resistance takes place when the thigh part 1 has at least an inertial angle $\alpha_T$ of at least 45°, in particular of at least 70°, and/or the knee angle $\alpha_K$ is greater than 45°, in particular greater than 80°. In general, when one or more of such angle variables occur, it can be assumed that the prosthesis user is in a seated position. This criterion can be supplemented by measuring the ground reaction force GRF. Generally, the ground reaction force GRF decreases significantly when the prosthesis user is sitting. Therefore, if the ground reaction force GRF is below a threshold value, this is a further factor in assessing whether or not a seated state is achieved.

An abrupt reduction in resistance, after defined threshold values have been reached, is often found to be unpleasant. Provision is therefore made that, after reaching a threshold value for the inertial angle $\alpha_T$ of the thigh part 1 and/or the knee angle $\alpha_K$, the resistance is reduced continuously with increasing inertial angle $\alpha_T$ and/or knee angle $\alpha_K$. Sitting down is assisted in this way, and the transition from standing to sitting made easier. The inertial angle $\alpha_T$ of the thigh part 1 can be determined directly by a corresponding sensor, or provision is alternatively made that the inertial angle $\alpha_T$ of the thigh part is determined from the inertial angle $\alpha_i$ of the lower leg part 2 and the knee angle $\alpha_K$.

If the thigh part 1 is located over a defined period of time in an inclined position, that is to say in a substantially horizontal state, such that the inertial angle $\alpha_T$ is between 70° and 110° for example, the resistance of the resistance device can likewise be reduced after a predefined time has elapsed, since it can then be assumed that the prosthesis user is seated or will not stand up again for a foreseeable time.

When the joint angle $\alpha_K$ or the inertial angle $\alpha_T$ of the thigh part 1 changes, the resistance can again be increased, preferably continuously increased, such that safety against falling back is provided, so as to make it easier for the patient to stand up. Moreover, provision can be made that a reduction in resistance is suppressed, even if the angle settings are present, as long as the patient moves the leg, that is to say if a change of joint angle, for example of the knee angle $\alpha_K$, is detected.

The invention claimed is:

1. A method for controlling an artificial orthotic or prosthetic joint of a lower extremity, comprising:
   providing a resistance device to which at least one actuator is assigned, via which actuator at least one of a flexion resistance and an extension resistance is changed depending on sensor data, with status information being made available via sensors during the use of the joint,
   reducing the at least one of a flexion resistance and an extension resistance after reaching an inertial angle of the thigh part of at least 45° to a vertical direction and the thigh part is located in an inclined position for a predefined period of time.

2. The method as claimed in claim 1, wherein the at least one of a flexion resistance and an extension resistance is reduced when a ground reaction force reaches or is below a threshold value.

3. The method as claimed in claim 1, wherein, after reaching a threshold value for the inertial angle of the thigh part, the at least one of a flexion resistance and an extension resistance is reduced continuously with increasing inertial angle.

4. The method as claimed in claim 1, wherein the inertial angle of the thigh part is determined directly or from the inertial angle of a lower leg part and a joint angle.

5. The method as claimed in claim 1, wherein, after being reduced, the at least one of a flexion resistance and an extension resistance is increased as a function of the inertial angle of the thigh part.

6. The method as claimed in claim 1, wherein a reduction in the at least one of a flexion resistance and an extension resistance is suppressed if a change of joint angle is determined.

7. The method as claimed in claim 1, wherein, after the at least one of a flexion resistance and an extension resistance has been reduced, an energy-saving mode is switched on.

8. The method as claimed in claim 1, wherein a plurality of control algorithms are present which, on the basis of measured values of different devices for detecting angles and forces, operate in such a way that, if a device for detecting angles and forces fails, the other measured values are used to control the change in the at least one of an extension resistance and a flexion resistance.

9. The method as claimed in claim 1, wherein reaching an inertial angle of the thigh part of at least 45° indicates a standing to sitting motion.

10. A method for controlling an artificial orthotic or prosthetic joint of a lower extremity, comprising:
    providing a resistance device, at least one actuator, and a plurality of sensors;
    changing at least one of a flexion resistance and an extension resistance with the actuator based on sensor data and status information provided by the plurality of sensors during use of the joint;
    measuring an inertial angle of a thigh part of the lower extremity relative to a vertical direction;

reducing the at least one of the flexion resistance and an extension resistance after reaching the inertial angle being at least 45° and the thigh part is located in an inclined position for a predefined period of time.

11. The method as claimed in claim 10, wherein the at least one of the flexion resistance and the extension resistance is reduced when a ground reaction force reaches or is below a threshold value.

12. The method as claimed in claim 10, wherein, after reaching a threshold value for at least one of the inertial angle and the knee angle, the at least one of the flexion resistance and the extension resistance is reduced continuously with increasing inertial angle and/or knee angle.

13. The method as claimed in claim 10, wherein the inertial angle of the thigh part is determined directly or from an inertial angle of a lower leg part and a joint angle.

14. The method as claimed in claim 10, wherein, after being reduced, the at least one of the flexion resistance and the extension resistance is increased as a function of at least one of the joint angle and the inertial angle.

15. The method as claimed in claim 10, wherein a reduction in the at least one of the flexion resistance and the extension resistance is suppressed if a change of joint angle is determined.

16. The method as claimed in claim 10, wherein, after the at least one of the flexion resistance and the extension resistance has been reduced, an energy-saving mode is switched on.

17. The method as claimed in claim 10, wherein a plurality of control algorithms are present which, on the basis of measured values of different devices for detecting angles and forces, operate in such a way that, if a device for detecting angles and forces fails, the other measured values are used to control the change in the at least one of the flexion resistance and the extension resistance.

* * * * *